United States Patent [19]

Ritota et al.

[11] 4,013,077
[45] Mar. 22, 1977

[54] COLLECTING DEVICE

[75] Inventors: Michael C. Ritota, Newark; L. Phillip Mancini, Bricktown, both of N.J.

[73] Assignee: M.E.D.S. Corporation, Newark, N.J.

[22] Filed: Feb. 6, 1976

[21] Appl. No.: 655,698

Related U.S. Application Data

[63] Continuation-in-part of Ser. No. 508,158, Sept. 23, 1974, Pat. No. 3,938,521, which is a continuation-in-part of Ser. No. 265,343, June 22, 1972, abandoned.

[52] U.S. Cl. .............................................. 128/295
[51] Int. Cl.² .......................................... A61F 5/44
[58] Field of Search ........... 128/1 R, 2 F, 129, 283, 128/295, 294, 349 B, 350 R, 246, 275–278

[56] References Cited

UNITED STATES PATENTS

| | | | |
|---|---|---|---|
| 2,819,718 | 1/1958 | Goldman | 128/350 |
| 3,353,538 | 11/1967 | Carrigan | 128/295 |

Primary Examiner—Robert W. Michell
Assistant Examiner—Henry S. Layton
Attorney, Agent, or Firm—Lerner, David, Littenberg & Samuel

[57] ABSTRACT

A collecting device for the collection of excretions from various body openings, both natural and surgical in nature, is disclosed. The collecting device includes an inflatable collar which may be inserted into a body opening prior to inflation, and then be inflated in order to firmly anchor itself within that opening and prevent its inadvertent removal therefrom, or attached to a body opening or appendage. A solid elongated tubular member is heat-sealed to either the inner diameter or outer diameter of the inflatable collar, and forms a continuous channel connecting the inflatable collar to a bag disposed external to the body opening so that body secretions from that opening are collected in the bag in a simple and hygienic manner. Means are thus provided for inflating the collar from a point external to the body opening after insertion, and channel means for connecting the inflatable collar to the means for inflating that collar, the channel means being located within the interior of the elongated tubular member and the bag itself, so that there is no contact between the channel means and the body opening upon insertion of the inflatable collar thereinto.

11 Claims, 19 Drawing Figures

COLLECTING DEVICE

REFERENCE TO RELATED APPLICATIONS

This application is a continuation-in-part of Ser. No. 508,158, filed Sept. 23, 1974, now U.S. Pat. No. 3,938,521, which in turn is a continuation-in-part of Ser. No. 265,343, filed on June 22, 1972, now abandoned, for a FECAL BAG, in the names of Michael C. Ritota and Louis P. Mancini.

BACKGROUND OF THE INVENTION

It has long been recognized that there are many patients in hospitals, nursing homes, and other such institutions, as well as invalided, deformed or crippled persons who are not toilet-trained or whose bowel movements, defecation and/or urinary functions are involuntary and uncontrolled so that their waste products cannot be contained or retained. Futhermore, there are many patients who have, as a result of various diseases, required the performance of an ostomy, whereby an exit for the feces is created before it reaches the rectum. This exit, known as a stoma, therefore requires a collecting device for use to collect feces exiting therefrom.

In addition, there are many female patients who have suffered various bladder infections, who have required the insertion of various tubes and other such means for collecting urine directly from their bladders. There are also many male patients who are physically disabled to the point where they are unable to leave their beds in order to urinate. In each of these cases, these unfortunate conditions exist for a variety of known reasons, and each is not only of great inconvenience to the patient or persons who suffer from them, but additionally present many problems such as unpleasant odors, unsanitary conditions, increased nursing care, and generally extreme discomfort to the patient.

Various devices have been developed in each of these situations in order to act as collecting devices for the excretions connected with each of the body openings discussed above. Thus, in the case of a fecal bag, U.S. Pat. No. 3,548,828 reveals a collecting appliance used in paraplegic and other bowel incontinent persons. This device, besides being impossible to produce commercially, suffers from many other serious shortcomings. Thus, the device of U.S. Pat. No. 3,548,828 cannot be inserted into the anus without causing extreme irritation to the patient, particularly since it does not present a smooth and regular surface to the body opening. In addition, this device suffers from other serious defects, such as leakage, etc. since it does not provide a smooth and/or continuous surface between the anchoring means 6 and the collecting bag 38. As can be seen clearly in FIGS. 3 and 4 of this patent, this device also requires that the patient have functioning sphincter muscles, and is adapted to contain an inflatable and deflatable adaptor means 12, quite apart from its anchoring means 6, which is inflated only during use, when the bag 38 is attached thereto, and which is deflated and closed by the functioning rectal sphincter muscles when the bag is removed and cap 36 is attached thereto. These difficulties which prevent the utilization of this device for patients who have completely lost control of these muscles, in addition to the extreme irritation caused by the neither smooth nor continuous outer surfaces of this device, particularly in view of tubes 22 and 19 which are used for inflation of its two inflatable portions, have rendered such devices totally useless.

Furthermore, the construction of these prior art devices have required the application of various adhesives in order to complete same, and the use of such materials in connection with such devices for insertion into the human body has been strictly forbidden by the Food and Drug Administration.

As for those patients who have had colostomies and require collection of fecal matter from a stoma, in the past this has been done by the adhesive attachment of various bags to the external surface of the stoma. These devices have therefore also resulted in serious consequences, including irritation and ulceration of the skin surface.

In connection with the collection of urine directly from a female bladder, this has, in the past, required the insertion of various devices directly into the bladder, and this has caused serious bladder infections. Specifically, the most commonly employed prior art device has included inflatable means for insertion directly into the bladder, and tubular means for removing urine therefrom. Again, insertion of any foreign matter into the bladder itself has consistently resulted in serious bladder infections. Similar problems have been encountered with respect to the collection of urine from bed-ridden male patients.

In connection with the application of enemas, such as barium enemas, this has in the past been extremely difficult, particularly with incontinent patients who cannot control or prevent the release of barium material prematurely.

Therefore, in each of these cases, there has been an extreme and urgent need for the development of a collecting device which overcomes these difficulties.

It is therefore an object of the present invention to provide a collecting bag which overcomes these and other problems associated with each of these prior art devices.

It is yet another object of the present invention to provide such a collecting device which is both sanitary and easily disposable, and which is relatively simple to use and sufficiently cheap to manufacture in order to meet the single use, throw-away concept of modern day medicine.

It is yet another object of the present invention to provide a collecting device which may be used continuously, and for long periods of time, without irritation to the body opening.

It is yet another object of the present invention to provide a collecting bag which can be easily replaced by relatively untrained individuals, without pain or other such difficulties to the patient, and which can be periodically inserted and removed without causing undue irritation or infection.

It is yet another object of the present invention to provide a collecting device which may be inserted into a stoma and employed by ostomy patients, with all of the above-noted advantages.

It is yet another object of the present invention to provide a collecting bag which may be employed by females for insertion into the urethra for collection of urine therefrom.

It is yet another object of the present invention to provide a collecting bag which may be reasonably employed for the collection of urine from bedridden male patients.

It is yet another object of the present invention to provide a collecting bag which helps eliminate odors and other such difficulties resulting from leakage associated with the involuntary and uncontrolled expelling of feces by such patients.

It is yet another object of the present invention to provide a collecting device which eliminates the transmission of bacteria and bacterial infections, and which can be used in connection with the analysis of excretions from various body openings.

It is yet another object of the present invention to provide a collecting bag which may be used as a fecal bag even where the defecation function of the rectal or sphincter muscles has been completely lost due to local disease, local inflammatory disease as in the case of typhoid, cholera, cholera or dysentery, central nervous system defects or disorders, or other reasons whereby there is still sufficient rigidity in the wall of the rectal ampulla to offer support for any structure inserted for engagement therewith.

It is yet another object of the present invention to provide a collecting device which may also be adapted to be used for the provision of an enema, such a barium enema, again with all of the above-noted advantages.

It is yet another object of the present invention to provide a method for manufacturing each of the above-noted collecting bags.

SUMMARY OF THE INVENTION

In accordance with the present invention a collecting device is provided for use in the continuous collection of excretions from various body openings, including an inflatable collar having an inner diameter and an outer diameter, an elongated tubular member attached to the inflatable collar, collecting means associated with the end of the elongated tubular member remote from the inflatable collar and means for inflating the collar.

In a preferred embodiment of the present invention, the collecting device is employed for the collection of urine from a male, and means for inflating the inflatable collar comprises valve means, and channel means are also provided for connecting the valve means to the inflatable collar. Preferably, the collecting means comprise bag means, and the elongated tubular member is attached to the outer diameter of the inflatable collar. In this embodiment, the channel means is preferably located within the interior of the bag means and the elongated tubular member. In addition, a semi-rigid member is maintained within the elongated tubular member to prevent its collapse.

In another embodiment of the present invention wherein the collecting device is employed for insertion into body openings, such as the anus, the elongated tubular member is attached to the inner diameter of the inflatable collar, and bag means are connected to the end of the elongated tubular member remote from the inflatable collar, so that the bag means is disposed exterior to the body opening upon insertion of the inflatable collar into that body opening. In this embodiment, means for inflating the collar are provided from a point external to said body opening when the inflatable collar has been inserted into that body opening, and channel means connecting the means for inflating the inflatable collar to the inflatable collar itself are provided within the interior of the bag means and of the elongated tubular member so that the channel means does not contact the body opening upon insertion of the inflatable collar into the body opening.

In another embodiment of the present invention wherein the collecting device is to be used as a fecal bag, the inflatable collar is prepared in a manner so that upon inflation and expansion thereof, frictional engagement with the ampulla wall of the rectum is provided to hold the fecal bag therein, so that the elongated tubular member extends through the anus, such that the bag means is located exterior thereto. Thus, the elongated tubular member forms a continuous channel from the inflatable collar to the bag means so that there is no leakage of any of the fecal matter to be collected during use thereof.

In another embodiment, where the collecting device is to be employed for insertion into a stoma, the inflatable collar will be of a length so that upon inflation a firm anchorage upon the surface of the colon is obtained. Additionally, in this embodiment, the elongated tubular member will be of a sufficient length to extend from the stoma to the bag means exterior thereto.

In yet another embodiment of the present invention, when the collecting bag of this invention is to be used as a urine collecting bag for females, the elongated tubular member will include a projecting tubular member which will be inserted into the urethra upon insertion of the inflatable collar into the vagina.

Further, in accordance with the present invention, a method for manufacturing such collecting devices comprising an inflatable collar and an elongated tubular member is provided, wherein the collecting device includes a smooth, continuous outer surface, and does not require the application of any adhesive in its construction, comprising preparing an inflatable collar by heat-sealing a first portion of said inflatable collar to a second portion of said inflatable collar, and attaching the inflatable collar to the elongated tubular member by heat-sealing the end of said tubular member to said inflatable collar. Preferably, the collecting means will also include bag means associated with the end of the elongated tubular member remote from the inflatable collar, and the bag means will include an internal channel or keyway attached to an inflating means at the remote end of said bag means from said elongated tubular member, and a tubular conduit will be heat-sealed to the upper portion of said inflatable collar for attachment to said keyway thus providing a channel for inflating and deflating the inflatable collar with air or a suitable liquid.

DETAILED DESCRIPTION

Figures 1, 2, 3, 4:
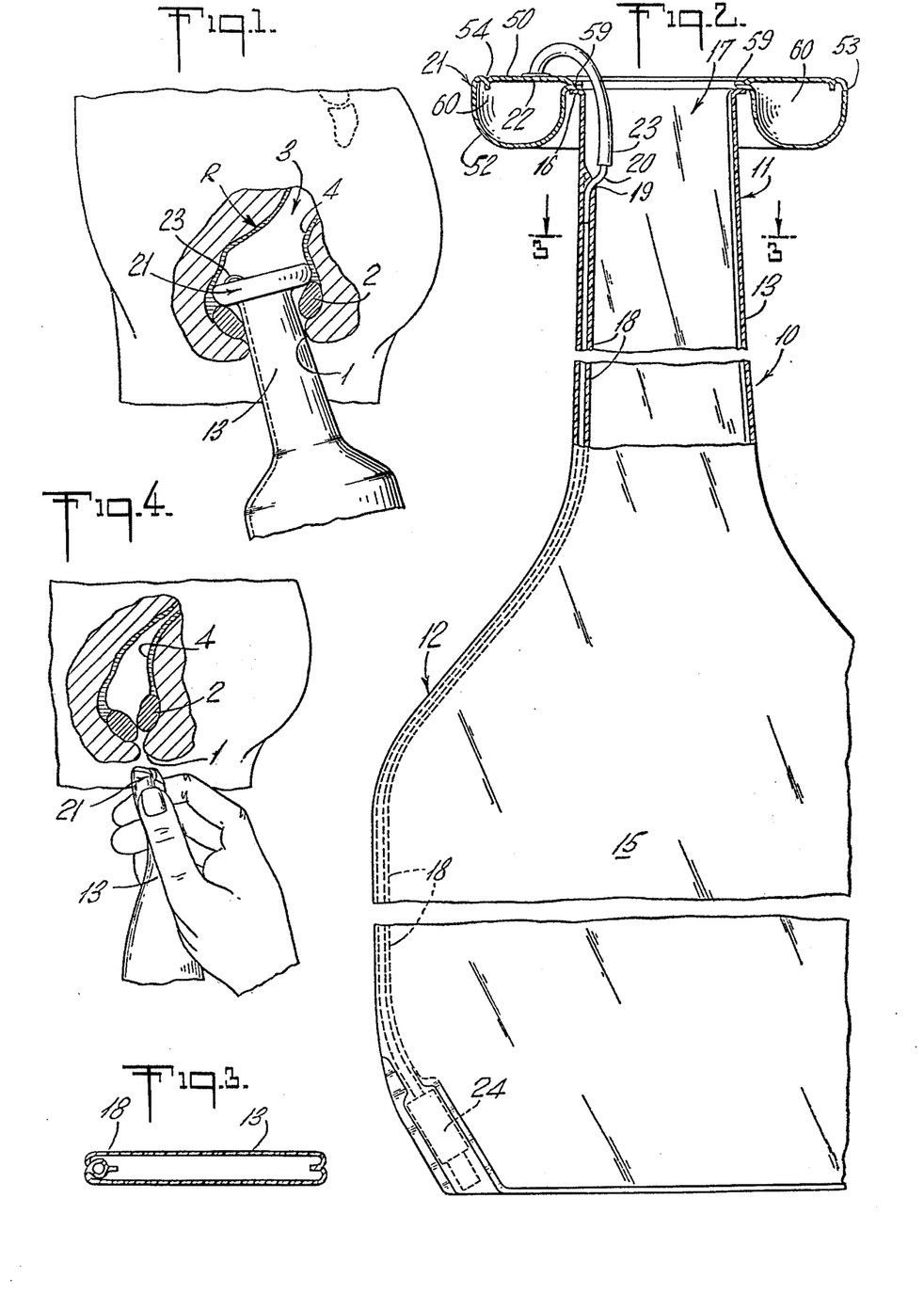
FIG. 1 is a side elevational, partially sectional view of a collecting bag of the present invention employed as a fecal bag, illustrated in assembled position in the rectum of a patient.
FIG. 2 is a side sectional elevational view of a collecting bag of the present invention.
FIG. 3 is a top elevational sectional view taken along section 3—3 of FIG. 2.
FIG. 4 is a side elevational partially sectional view showing manual insertion of the deflated inflatable collar of the collecting bag of the present invention into the rectum.

Referring to the drawings, in which like numerals refer to like portions thereof, FIG. 1 shows a fecal bag of the present invention assembled and inserted into the patient's rectum. The configuration of the rectum generally designated R of the patient includes the anal opening or anus 1 provided with rectal or sphincter muscle generally designated 2 which in normal operation acts to hold the rectum closed. Inwardly of the anus the rectal passage 3 forms an enlarged space or ampulla 4 and then extends further into the body for connection to the end of the large intestine (not shown).

While the ampulla 4 of the rectal passage 3 is enlarged the wall thereof has sufficient rigidity, even where a complete loss of control of the sphincter muscle 2 has occurred, to permit frictional engagement therewith of a fecal bag device in accordance with the present invention, to be fully described below. In addition, since the collecting device of this invention provides a smooth, continuous outer surface, particularly with respect to that portion thereof which is inserted with the rectum R, there is no irritation whatsoever between the collecting device and the anus 1 of other portions of the rectum R.

Thus, referring to FIG. 2, a collecting device, which in this drawing may be the fecal bag shown in FIG. 1, is generally designated 10, and generally has a unitary construction. The fecal bag 10 thus includes an insertable section 11 and a collecting section 12.

The insertable section 11 consists of an elongated tubular member 13, which, as shown in FIG. 1, will have a length sufficient to permit a portion thereof to extend external of the rectum when the insertable section 11 is disposed in assembled position, as shown in FIG. 1. The elongated tubular member 13 is preferably made of a medically approved, thin, pliable material such as a medically approved plastic, in the form of films of up to 8 mils or sheets of greater thickness, and having sufficient stiffness or sufficient strength to permit the insertable section to be passed through the anal opening into the rectum either by manual insertion as by squeezing the elongated neck together as illustrated in FIG. 4, or by means of some suitable insertion instrument. The ease of insertion may thus be facilitated by lubricants, oil or vaseline, or any other similar type substances which have no adverse effects upon the patient.

Materials which are presently medically approved include various plastics, as well as certain silicon compounds, such as the product sold on the open market under the trademark SILASTIC S-2000. Of the medically approved plastics or rubbers, such as urethane, polyvinyl-chloride (PVC) and Kraton rubber are preferred because of their heat sealing properties, with PVC being particularly preferred.

In the case of the fecal bag shown in FIG. 2, the diameter of the elongated tubular member 13 will be in the range of from about 1 inch to about 1½ inches, which is the approximate maximum degree to which the anus will expand under normal pressure or under conditions where control of the rectal sphincter muscles has been completely lost. The length of the elongated tubular member will generally be in a range from about 2½ inches to about 4 inches, with an average length of about 3 inches.

The significance of this diameter and length is noted because the elongated tubular member 13 forms a connecting passage between the bag or collecting means 12 and the inflatable collar, generally designated 21.

Figure 10:
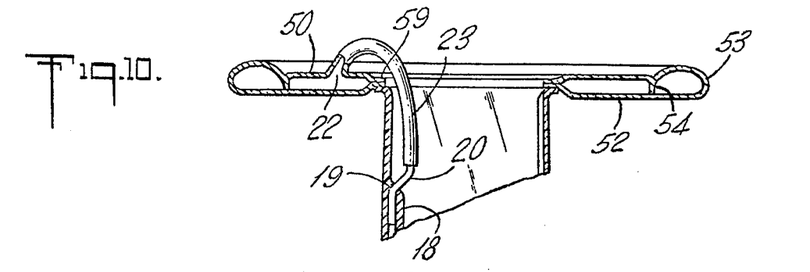
FIG. 10 is a partial sectional view of an inflatable collar of the collecting bag of the present invention, in deflated orientation.
Figure 11:
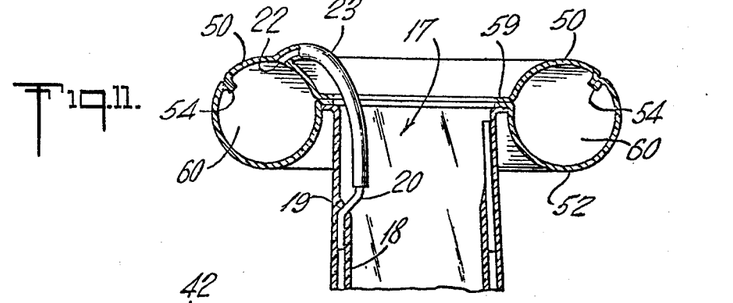
FIG. 11 is a partial sectional side view of an inflatable collar of the collecting bag of the present invention, in inflated orientation.

The inflatable collar 21 itself, as can best be seen in FIGS. 2, 10 and 11, includes a first annular portion 50, and a second portion 51 including an annular portion 52, and a flange-like portion 53 which becomes substantially perpendicular to the annular portion 52 upon inflation, as shown in FIG. 11, thus forming a cup-like member about an inner aperture 49. These two portions are heat-sealed together at heat-sealed joint 54 in order to form the inflatable collar, as will be discussed in more detail below with respect to the method of manufacturing the collecting bag of the present invention. Thus, since the annular portion 50 includes an inner diameter 56 and an outer diameter 58, and the second portion 51 of the inflatable collar 20 includes an inner diameter 57, upon heat-sealing of the substantially coextensive diameters 56 and 57 together, as shown at 59, an annular space 60 is formed, which annular space may now be inflated.

The collecting section 12 of this collecting device of the present invention includes a bag portion 15 and the elongated tubular member 13. At the end of the elongated tubular member 13 remote from the bag 15 the inflatable collar 21 is attached. This is accomplished by means of heat seals at circular flange 16 (see FIG. 2) thus sealing the ends 58 and 53 of the first member 50 and the second member 52 of the inflatable collar 21 to the annular flange 16, at 59. In this manner, a smooth, continuous outer surface is provided from the inflatable collar 21, which is inserted into the body opening such as the anus, through the elongated tubular member 13, which extends into that body opening, and finally to the bag 15 which is located external from the body opening.

In order to pass any liquid, air or other gas to or from the annular space 60 within the inflatable collar 21, for the purpose of inflating same, a conduit is provided. Thus, keyway 18 is provided within the interior of the collecting section 12, running from the upper portion of the elongated tubular member 13 along the inner wall of the collecting section 12, through bag 15, along its inner wall, as shown in FIGS. 2 and 3. The upper portion of keyway 18 ends in opening 19, into which is inserted tubular connector 20. The inflatable collar 21 is provided with an opening 22 to which is heat-sealed tubular conduit 23. The tubular connector 20 is inserted into the opposite end of tubular conduit 23 from that end which is heat-sealed to the opening 22 in the inflatable collar 21, so that a continuous closed passage is provided from the annular space 60 of the inflatable collar 21 through tubular conduit 23, tubular connector 20, and keyway 18, to the remote portion of bag 15. The outer diameter of tubular connector 20 must therefore be slightly smaller than the inner diameter of tubular conduit 23, so that it can fit snugly and permanently therein. At the bottom of bag 15 is provided a suitable bi-directional control valve means generally designated 24 which is thus readily available at a location exterior of the body opening when the collecting device is in the assembled position, such as in the rectum as shown in FIG. 1 of the drawings. Most significantly, this entire apparatus which provided for the inflation and deflation of inflatable collar 21 is provided in a manner such that the smooth continuous outer surface of the collecting bag 10 is uneffected, so that there is no contact whatsoever between the body opening, such as anus 1, and the means for inflating and deflating inflatable collar 21, including channel or keyway 18.

Figure 13:
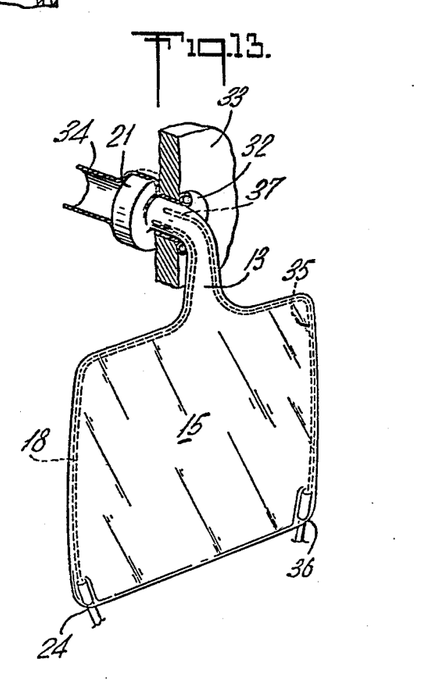
FIG. 13 is a partial elevational view of another collecting bag of the present invention shown inserted in assembled position in a stoma.

Referring now to FIG. 13, an embodiment of the collecting device of the present invention for use by patients who have had an ostomy, and who therefore now possess a stoma, is shown. In this embodiment, the main features of the collecting bag as described above with reference to a fecal bag for insertion in the anus are identical. However, for use in this application, it is necessary to modify the collecting bag, such as by altering the actual dimensions of inflatable collar 21 and elongated tubular member 13, in order to fit the particular circumstances of this use. Generally, a somewhat longer inflatable collar 21 is provided in connection with this application, since somewhat greater holding power may be required.

Thus, as shown in FIG. 13, in the situation where the patient has undergone a colostomy, and has been provided with a stoma 32, in his abdomen 33, which now functions as a replacement for his rectum, it again becomes necessary to attach a collecting device in order to accomplish the results described above. As is shown in FIG. 13, the collecting device of the present invention is inserted through the stoma 32 prior to inflation, and upon inflation of the inflatable collar 21 therewithin, the wall of the colon 34 is expanded at the point of contact with the inflatable collar 21 so that the collecting bag is firmly anchored within the stoma 32. The elongated tubular member 13 thus extends from the stoma and the bag itself is fully exterior thereto. Again, a smooth unbroken surface is presented to the wall of the stoma and through the abdomen 33 so that no irritation whatsoever is caused thereupon. Again, the means for inflation of the inflatable collar 21 includes keyway 18 which is furnished along the inner wall of the elongated tubular member 13 and the bag 15, attached to valve member 24 at its end remote from the body opening or stoma 32, and to the inflatable collar in the manner shown in FIGS. 10 and 11, and described above, at its other end within the body opening. As can also be seen in FIG. 13, the bag portion 15 itself is of a somewhat shorter, wider shape in this case, again merely for purposes of convenience to the patient, etc.

An additional embodiment of the present invention is also shown in FIG. 13, and includes an additional keyway 35. While this embodiment will now be discussed, it should be noted that while it is only shown in conjunction with the collecting device for use in conjunction with a stoma, it is fully applicable to the fecal bag described above. This embodiment, including keyway 35 disposed within the collecting device along the inner surface of the elongated tubular member 13 and the bag 15, provides for the application of an enema through the collecting device of the present invention without interfering with its primary purpose as described herein, and with ease and speed. The keyway 35 thus terminates in a cockpit 36 which may thus be connected to an enema dispensing bag. Thus, for example in the application of a barium enema, the barium liquid contained in a dispensing bag is attached to cockpit 36 and applied therethrough, generally by gravity feed. At the end of the keyway 35 remote from this cockpit 36, a simple tubular opening 37 is provided within the end of the elongated tubular member adjacent the inflatable collar 21 so that the liquid is directed directly into the colon 34. It should also be understood that in place of keyway 35 a simple tube means may be provided within the collecting bag, preferably wider than the keyway shown in the drawings. At this point the elongated tubular member 13 of the collecting bag may be tied off, and in the case of a barium enema, the necessary X-rays, etc. may be taken. More particularly, however, in the case of a barium enema and the like, a clamp or clip extending across the tubular member but not across the barium enema keyway will be used. Thus, in cases where the patient rejects the barium, such as by an involuntary muscular spasm and the like, the barium will not be rejected into the collecting bag, and at the same time the insertion of barium through the keyway will not be halted or interferred with. The tied-off portion may then be released, permitting the barium, or other enemator, to flow into the collecting bag.

Figure 12:
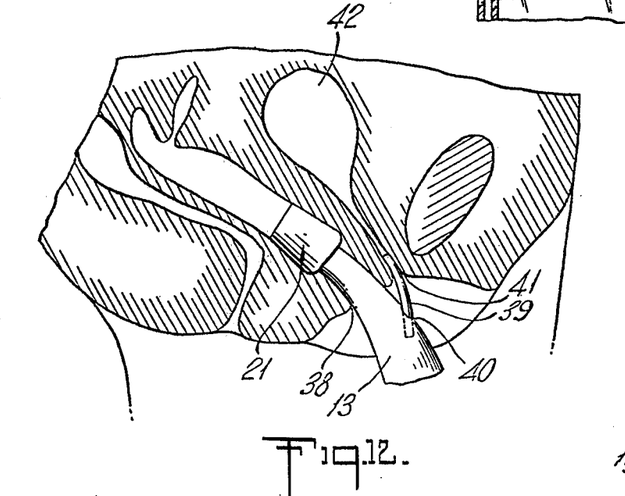
FIG. 12 is a perspective view of a portion of another form of a collecting bag of the present invention inserted into a vagina and a bladder.

Yet another embodiment of the present invention is shown in FIG. 12 hereof. In this embodiment, all of the essential features of the collecting bag described above are again included herein, including the inflatable collar 21, elongated tubular member 12, and the collecting bag itself. While each of these is thus identical in principal to that described above, the actual function of this collecting bag is somewhat different. Also, the inflatable collar and bag may again be somewhat modified in shape or design, such as by further lengthening the inflatable collar 21 for firmer anchorage, etc. Thus, in this case, while the deflated collar and elongated tubular member are inserted into the vagina 38 upon inflation, the purpose of this insertion is merely for such anchoring, and not for any actual collection of excretions through the opening 17 into the elongated tubular member 13, as is the case in the collecting bags described heretofore. Although the bag 15 itself is used for collecting urine, collecting occurs through a separate semi-rigid tubular member 39 which is attached through an opening 40 in the elongated tubular member 13. In this manner, the semi-rigid tubular member 39 projects from the elongated tubular member 13 a substantial distance into the urethra 41, so that it can now collect any urine discharged from the bladder 42, without actually entering the bladder 42. This material then passes through the semi-rigid tubular member 39 into the collecting bag. In this manner, where such collection becomes necessary due to local infection, etc., collection is accomplished without causing greater infection or irritation, in a simple and expedient manner.

Figure 14:
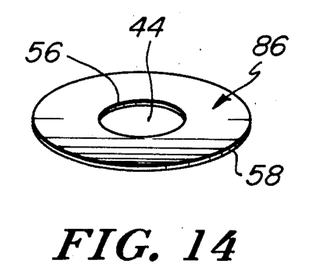
FIG. 14 is a plan view of another first portion of the inflatable collar of the present invention.
Figure 16:
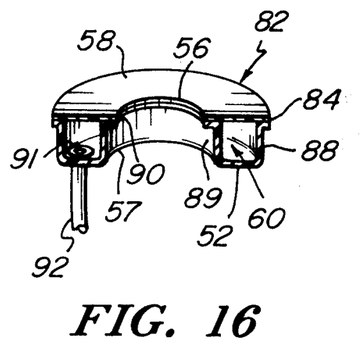
FIG. 16 is a partial plan view of the other first and second portions of the inflatable collar of the present invention in partially sealed relationship.
Figure 17:
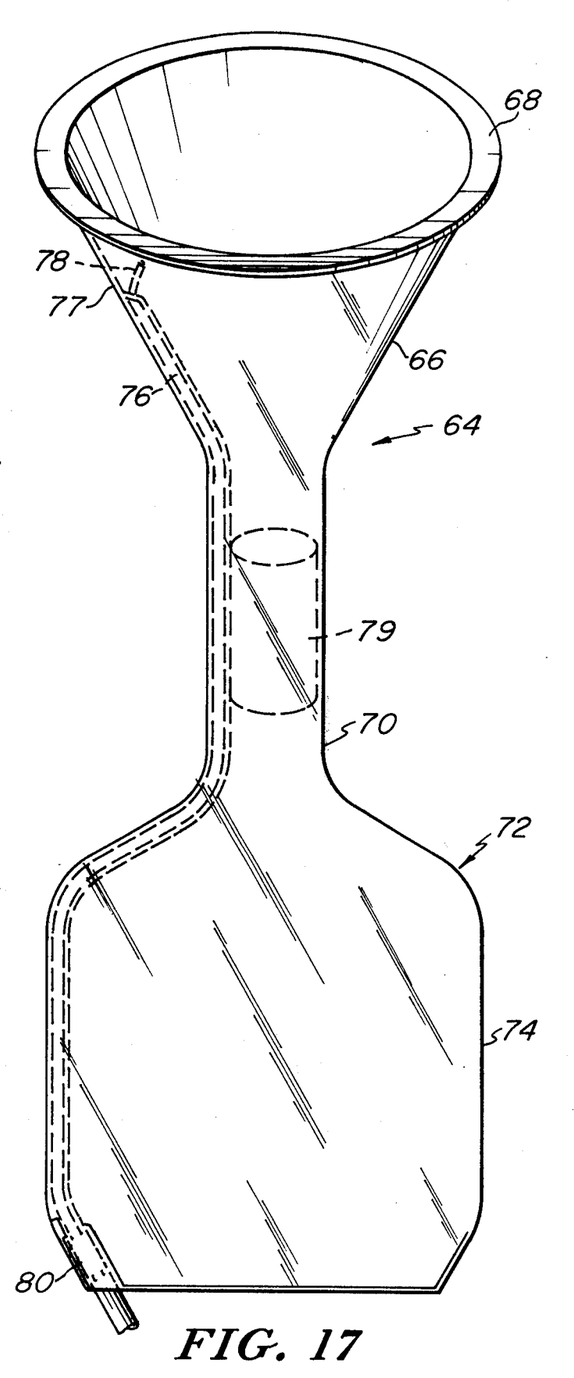
FIG. 17 is a side elevational view, partly broken away, of the bag portion of another collecting bag of the present invention.
Figure 18:
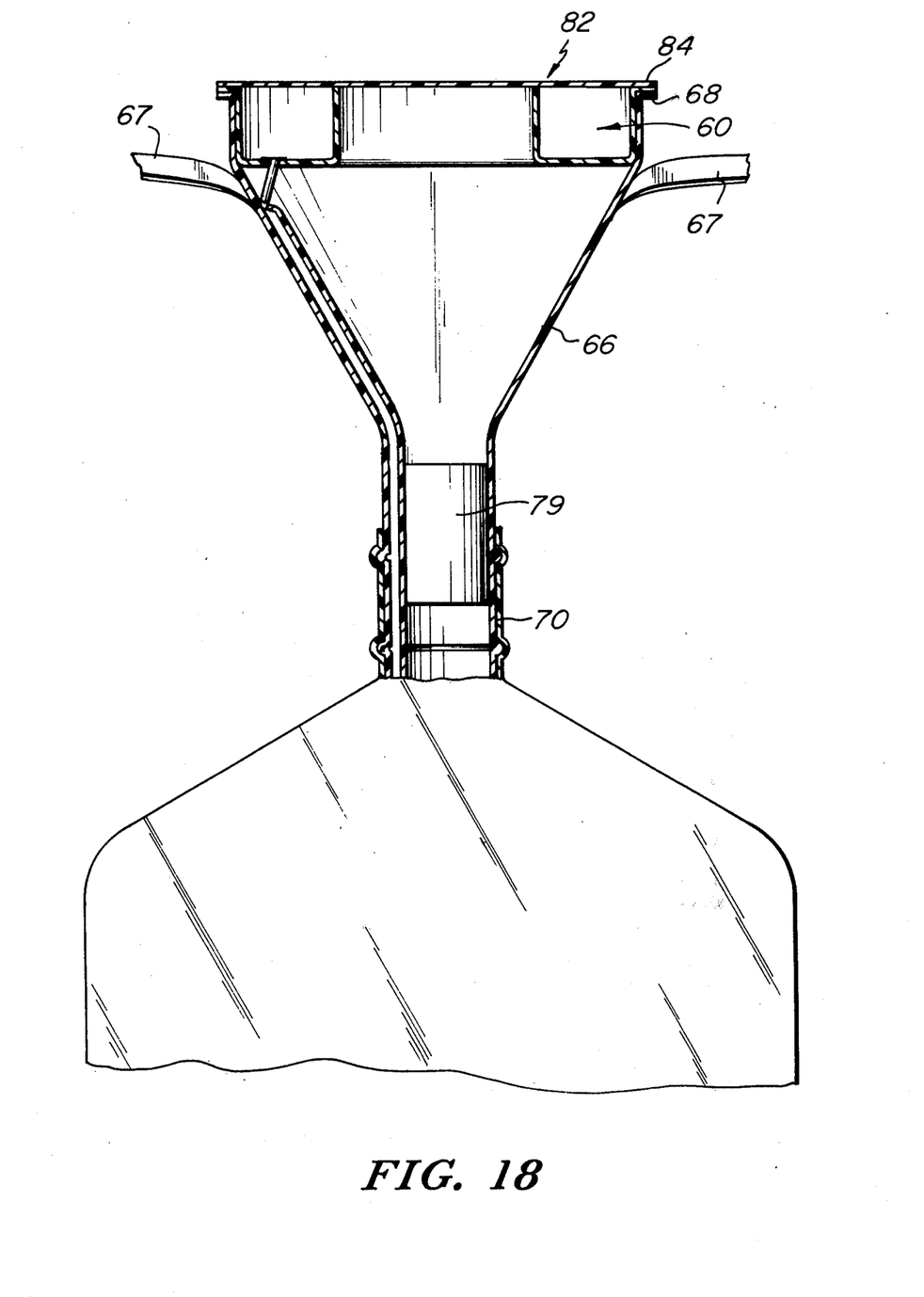
FIG. 18 is a partial side elevational view, partly broken away, of another collecting bag of the present invention.

In another embodiment of the present invention, as shown specifically in FIGS. 17 and 18, the collecting device of the present invention may be employed, in a slightly modified form, for the collection of urine from a male. In this embodiment, while the choice of material and many of the features are modified in accordance with this particular use, the device again includes an inflatable collar and an elongated tubular member attached thereto. However, in this application, the elongated tubular member is heat sealed to the outer diameter of the inflatable collar, and the inflatable collar itself is preferably manufactured in a manner to be discussed more fully below, with reference to FIGS. 14 through 16 hereof. In any event, this embodiment may include a bag means associated with the end of the elongated tubular member, or may include a lengthy elongated tubular member for collecting purposes, and no separate bag means, or a removable bag means associated therewith.

With reference to FIG. 17, the elongated tubular member 64 includes a conical upper portion 66 which terminates in an upper flange portion 68, which will be described in more detail below with respect to the method of heat sealing the inflatable collar thereto. The elongated tubular member then includes a neck portion 70 depending therefrom. While the collecting means of this embodiment may thus terminate at the end of neck portion 70, it is also possible to include a bag means 72 either for removable attachment to the end of neck portion 70 as shown in FIG. 17, or in continuous manner attached to that neck portion, as in the case with the collecting bags described previously. In the embodiment shown in FIG. 17, the bag means 72 includes a bag portion 74, which again may have a modified shape in accordance with the particular useage in question. Furthermore, both the conical portion 66 and the neck portion 70 of the elongated tubular member may include an internal keyway 76 therewithin, also in accordance with the keyways described above. This keyway may therefore end at 77, and a tubular connecting member 78 may be inserted thereinto, further in accordance with the discussion below with regard to the inflatable collar for use herewith. In addition, it is preferable to include a rigid or semi-rigid cylindrical member 79 within the neck portion 70 of the elongated tubular member 64, in order to maintain this portion of the elongated tubular member open, and to prevent its collapse during use, therefore not permitting a liquid to flow therewithin. Again, valve means 80 may be attached to the end of keyway 76, also in accordance with the discussion above with respect to valve 24.

With reference to FIG. 18, an inflatable collar 82 is shown in connection with this embodiment, that is attached to the upper portion of the conical portion 66 of elongated tubular member 64 thereof. The inflatable collar 82 thus includes a heat sealed joint 84 which, in turn, is heat sealed to flange 68. In this regard, with reference to FIGS. 14 through 16 and FIG. 18, the inflatable collar includes a first annular portion 86, similar to first annular portion 50 shown in FIG. 5, but not including either opening 22 or tubular conduit 23 therein. Therefore this member merely includes an inner diameter 56 and an outer diameter 58, as well as central opening 44 therein. Inflatable collar 82 also includes a second annular portion 87, including annular portion 52, as in the embodiment shown in FIG. 6, and two flange-like portions 88 and 89, 88 at the outer diameter of the flange-like member 52 and 89 at the inner diameter thereof, surrounding inner aperture 49. These two portions are heat sealed together at heat sealed joint 84 in order to form the inflatable collar, as will be discussed in more detail below with respect to the method of manufacturing the collecting bag of the present invention. Furthermore, the flange 90 of the inner flange-like member 89 is heat sealed to the inner diameter 56 of the first annular member 86, thus forming the complete closed inflatable collar, including annular space 60 formed therein. The second annular member 87 includes an opening 91, to which is heat sealed tubular conduit 92, as shown in FIG. 16, and therefore the end of tubular conduit 78 may be inserted into the end of tubular conduit 92 in order to form a continuous closed passage from the annular space 60 of the inflatable collar 82 through tubular conduits 78 and 92. Other structures for inflating inflatable collar 82 are discussed below. In addition, a pair of straps 67, preferably prepared from a thin plastic material, is heat sealed to the conical portion 66, so that the entire collecting bag may be more firmly secured to the patent by tying same around his body.

Figure 5:
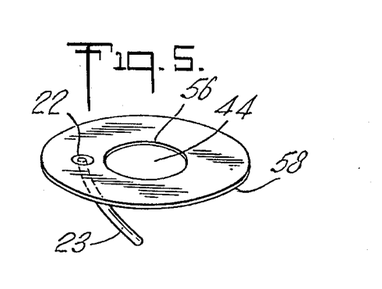
FIG. 5 is a plan view of a first portion of the inflatable collar of the present invention.
Figure 6:
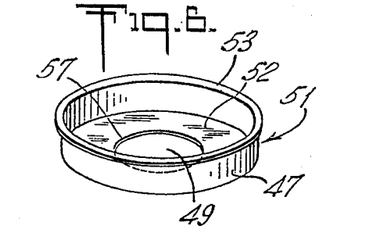
FIG. 6 is a plan view of a second portion of the inflatable collar of the present invention.
Figure 7:
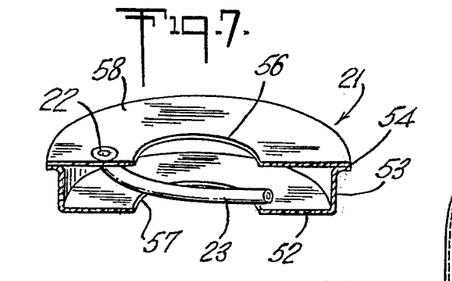
FIG. 7 is a partial plan view of the first and second portions of the inflatable collar of the present invention in sealed relationship.
Figure 8:
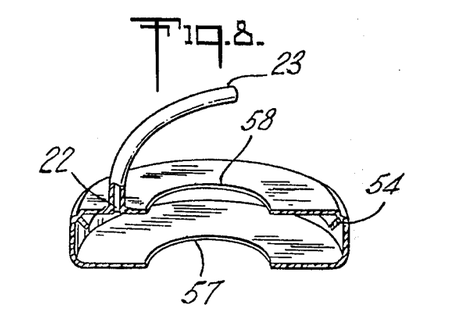
FIG. 8 is a partial plan view of the inverted inflatable collar of FIG. 7.

Referring now to FIGS. 5 through 9, one method of the manufacture of a collecting bag of the present invention will now be described. This method of manufacture thus results in the preparation of a collecting bag having a smooth, continuous outer surface, and one which does not require the application of any adhesive in order to construct same. The latter factor is of extreme significance in those medical applications wherein the collecting device is to be inserted into a body opening since the appropriate government authorities will not permit such devices to result in the insertion of any adhesive joints into any of the body openings in question. Throughout this description it should be realized that the entire collecting bag, including all of its components will preferably be prepared from a thin, medically-approved pliable plastic or rubber material, such as Kraton rubber, PVC or urethane plastics, having the required heat-sealing properties, and preferably these materials will be greater than 8 mils thick, such as from 8 to 12 mils thick. Referring specifically to FIG. 5, a first portion 50 of the inflatable collar of the collecting device of the present invention is initially provided. This first portion comprises an annular disc, including an opening 44 therethrough, which will eventually act as the entrance port for collecting the excretion associated with the particular body opening with which the specific collecting bag to be manufactured is to be used. This first annular portion 50 of the inflatable collar 21 thus includes an inner diameter 56 and an outer diameter 58, and may itself be prepared by application of a die upon a flat film or sheet of the plastic material. The initial step in the preparation of the collecting device of this invention thus comprises the application of a tubular conduit 23 to this first annular portion 50. This application of the tubular conduit 23 is accomplished by heat-sealing the end of tubular conduit 23 to one surface of this annular disc 50, as shown in FIG. 5, and by providing an opening 22 at the point of application, between the inner diameter 56 and the outer diameter 58 of the first portion 50 of inflatable collar 21. A second portion 52 of the inflatable collar 21 is shown in FIG. 6. This portion generally comprises an annular disc portion 52 and a transverse flange portion 47 extending perpendicularly from the outer diameter thereof. This second portion 52 of the inflatable collar 12 thus is of a dish shape, including a circular opening 49 therein corresponding to the opening 44 in the first portion 50 of the inflatable collar. This second portion 52 itself is prepared from a flat sheet of the plastic material to be employed by vacuum forming this portion 52 into the shape shown in FIG. 6 employing male and female die portions which are applied against the slightly heat softened plastic material. In order to prepare the inflatable collar 21, the first portion 50 and the second portion 51 are joined together by merely placing the first portion 50 upon the outer rim 53 of the transverse portion 47 of the second portion 52 and heat-sealing the outer diameter 58 of the first portion 50 to the outer flange 53 of the second portion 51, in order to prepare the inflatable collar as shown in FIG. 7. The heat-sealed joint is thus shown as 54 in that Figure. Subsequently, the entire inflatable collar 21 as shown in FIG. 7 is inverted, into the position shown in FIG. 8. In this manner the heat-sealed joint 54, which may now be trimmed, is now located within the interior of the inflatable collar, as shown in FIG. 8, and the tubular conduit 23 is located on the exterior of the upper surface thereof. It can now be seen that the final inflatable collar, including annular space 60, may be prepared by heat-sealing together the corresponding inner diameters 57 and 58, into the configuration shown in FIGS. 10 and 11, where this heat-sealed portion is shown at 59. There is thus provided a completely closed annular collar, including an entrance port 22 connected to conduit 21 for the injection of air or suitable liquid for inflation of the collar. The last step, however, is preferably accomplished at the same time that the inflatable collar 21 is applied to the remaining portion of the collecting bag 15, as discussed below.

Figure 9:
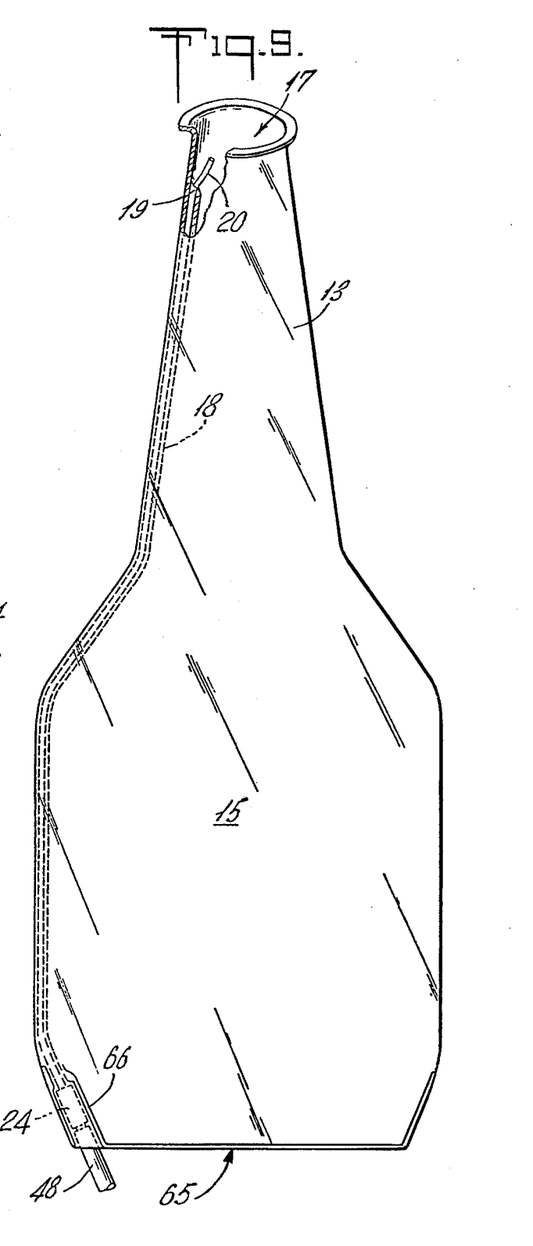
FIG. 9 is a side elevational view, partly broken away, of the bag portion of a collecting bag of the present invention.

The remaining portion of the collecting device of the present invention, as shown in FIG. 9, includes the bag portion 15 and the elongated tubular member 13. While the elongated tubular member 13 is shown as conical in shape in FIG. 9, it also may be cylindrical, as this shape is merely a matter of choice, depending on the particular circumstances and use required. This portion of the collecting bag of the present invention may itself be prepared from two flat films or sheets of plastic material to be employed. These two sheets are laid side by side, and appropriate dies are applied to the surface thereof. The dies heat-seal the two flat sheets together in the shape of the bag which is desired. In addition, the keyway 18 may also be applied to the inside of the bag at the same time by applying an additional heat seal along the inner wall of keyway 18, so that the keyway itself is provided between this inner heat seal and the outer heat seal of the bag itself. The keyway 18 thus extends almost to the end of the elongated tubular member 13. Furthermore, at this point, it is preferred to heat-seal only the two side portions of the collecting bag 15, leaving the bottom portion 65 open and unsealed. Further, a pocket 66 may also be formed at the bottom end 65 of the collecting bag 15 at this point, for subsequent insertion of valve 24 thereinto. In addition, tubular conduit 20 may now be attached to opening 19 at the end of keyway 18 adjacent the open end 17 of the elongated tubular member 13. In order to finally prepare the finished collecting device, the inflatable collar as shown in FIG. 8 is placed atop the end of the elongated tubular member 13, upon flange 16, and the three corresponding circular portions, represented by flange 16, and inner diameters 57 and 58, are heat sealed together as shown in FIGS. 10 and 11, at 59. The actual heat sealing of the inflatable collar 21 to the elongated tubular member 13 of bag 15 may thus be accomplished by placing the entire bag as shown in FIG. 9 over a die or mandrel, through the open end at the bottom 65 of the bag. The end at flange 16 of the elongated tubular member 13 is thus draped over the end of the mandrel a short distance, and the inflatable collar 21 in the condition shown in FIG. 8 may thus be applied directly to that flange by heat sealing thereto in the manner described above. In order to finalize the bag it is therefore only necessary to close off the bottom 65 of the bag 15 by heat sealing the two sheets of plastic together at that point along the bottom edge thereof, and then inserting valve 24 into pocket 66 performed during the initial heat-sealing of the two flat sheets of plastic into the bag 15 itself. Finally, tubular member 20 may be inserted into tubular conduit 23, thus completing the closed connection between the annular chamber 60 of the inflatable collar 21 through keyway 18 to valve 24.

A unitary continuous collecting device, having a smooth continuous outer surface, including means for inflating and deflating the inflatable collar, which is entirely enclosed within the collecting bag, is thus provided.

It should also be understood that while the form of the invention shown in the drawings has such a unitary construction, it is also possible to provide a detachable collecting section, so that the inflatable collar and the upper portion of the elongated tubular member 13 may be in-dwelling, and the collecting section, including the bag 15 and the lower portion of the elongated tubular member 13 may be removable and replaceable. In this form of the invention, the construction is identical. In this construction, the two piece form of the collecting bag includes a divided elongated tubular member, such that the upper portion thereof is provided with a connecting member, which co-operates with a connecting member similarly attached to the lower portion of the elongated tubular member, including the bag 15. This may be accomplished by means of mating surfaces, such as a shoulder, or an outer flange. In particular, as shown in FIG. 18, the elongated tubular member 70 associated with the bag, is disposed over the elongated tubular member associated with the inflatable collar 82, specifically employing a strip of plastic heat-sealed to the outer surface of this upper elongated tubular member, preferably at the location of the cylindrical member 79.

Figure 15:
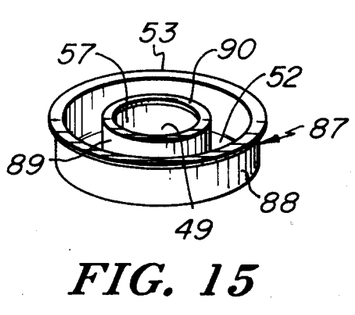
FIG. 15 is a plan view of another second portion of the inflatable collar of the present invention.
Figure 15A:
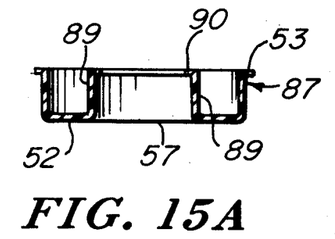
FIG. 15A is a side, sectional view of the FIG. 15.

Referring now to FIGS. 14 through 17, another method of the manufacture of a collecting device of the present invention is shown, and will now be described. This particular method of manufacture results in the collecting device described above with respect to the collection of urine from a male. In this particular application, since the device itself will not be inserted into any body openings, some of the prohibitions previously discussed with respect to the use of adhesives, etc., are not nearly as critical. In any event, referring specifically to FIG. 14, a first portion 86 of the inflatable collar designated by number 82 in FIG. 18 is shown. This first portion comprises an annular disc, including an opening 44 therethrough, as previously discussed. This first annular portion of inflatable collar 82 thus includes an inner diameter 56 and an outer diameter 58, and may again be prepared by application of a die upon a flat film or sheet of the plastic material utilized. This disc does not include either opening 22 or tubular conduit 23, as in the device shown in FIG. 5 and disclosed previously. A second portion 87 of the inflatable collar 82 is shown in FIG. 15. This portion generally comprises an annular disc portion 52 and a pair of transverse flange portions 88 and 89, extending perpendicularly from the outer and inner diameters, respectively, thereof. This second portion 87 of the inflatable collar 82 is thus of a generally U-shaped configuration, including a central circular opening 49 therein corresponding to the opening 44 in the first portion 86 of the inflatable collar. This second portion 87 itself is prepared from a flat sheet of the plastic material to be employed by vacuum forming this portion into the shape shown in FIG. 15 employing male and female die portion which are applied against the slightly heat-softened plastic material.

In order to prepare inflatable collar 82 from these two portions thereof, they are joined together by placing the first portion 86 upon the outer rim 53 of the outer transverse wall member 88 and upon the rim 90 of the inner transverse wall member 89, so that the openings 44 and 49 are in alignment, and heat sealing the outer diameter 58 of the first portion 86 to the outer flange 53 of the transverse wall member 88 of the second portion 87, in order to prepare the inflatable collar as shown in FIG. 16. In addition, the inner diameter 56 is similarly heat sealed to the inner flange 90 of the inner transverse wall member 89, thus forming a sealed inner chamber 60 therewithin. Subsequently, tubular conduit 92 can then be applied to the second annular member 52 by heat-sealing the end of the tubular conduit 92 to one surface of this annular disc 52, as shown in FIG. 16, and by providing an opening 91 at the point of application. Preferably, in preparing the closed inflatable collar 82 as shown in FIG. 16, the inner seal at rim 90 may be trimmed subsequent to heat sealing to remove excess plastic therefrom. On the other hand, the outer heat seal at 84 is not trimmed for the reasons discussed below.

It can now be seen that the inflatable collar 82 may be attached to the end of the elongated tubular member, including flange 68 as seen in FIG. 17, by merely placing the outer diameter of the inflatable collar, including heat seal location 84 upon flange 68 and heat sealing these together, as can be seen best in FIG. 18. The prior method of preparing the elongated tubular member, with or without associated bag means applies equally as well with respect to this particular method of manufacturing this particular collecting device.

The collecting device of this invention may also be provided with a clamp or tie-off means which merely includes such a clamp, string, tape or other means so that upon removal of the collecting device, the elongated tubular member may be sealed off for sanitary purposes, or as discussed above, clamps off any part of the elongated tubular member, still permitting entry of fluid via the enema keyway, etc. Although the use of the collecting bag of this invention will now be obvious from the above description, simple reference is made to typical usage of same. Thus, particularly referring to FIG. 4 hereof, the end of the elongated tubular member, including the deflated inflatable collar 21, is squeezed together, particularly because of its preparation from a suitable pliable material, and manually grasped as shown by the hand in FIG. 4. After suitable lubrication this insertable section may thus be inserted into the body opening, such as the rectum shown in FIG. 4. This section is then moved into the rectum until the inlet opening of the elongated tubular member 13 lies closely adjacent to the inner wall of the ampulla of the rectum. When the collecting bag is in this position, any suitable liquid or gaseous means, such as air, is connected to the valve 24 as shown by connecting means 48 in FIG. 9, and the inflatable collar is inflated. As the inflatable collar 21 expands, it presses against the wall of the ampulla, and becomes firmly anchored therewithin, irrespective of the condition of the sphincter muscles 2.

The collecting bag may thus remain in position until it is desired to remove the device from the patient, and at that time by manipulating the valve, the water, air or other gas in the inflatable collar 21 can be allowed to escape, and since nothing now holds the collecting bag in the assembled position in the rectum, the fecal bag can be easily removed by sliding it therefrom.

The foregoing is considered as merely illustrative of the principals of the present invention. Changes and alterations will readily occur to those skilled in this art from the above disclosure, and it is therefore not desired to limit the invention to the exact construction described and all suitable modifications and equivalents are deemed to be covered by the scope of the invention as now claimed.

What is claimed is:

1. A urine-collecting device for use in the continuous collection of urine from a male penis, comprising
   a. an inflatable collar for attachment to a penis, so that upon its inflation, said collar is firmly anchored to said penis said inflatable collar including a first annular member having an inner and outer diameter and a second annular member having an inner and outer diameter, said second annular member being substantially U-shaped in configuration upon its inflation, said inner diameter of said first annular member and said inner diameter of said second annular member being sealingly attached, and said outer diameter of said first annular member and said outer diameter of said second annular member being sealingly attached, thus forming said closed annular space therebetween, said sealingly attached outer diameters of said first annular member and said second annular member forming the outer diameter of said inflatable collar,
   b. an elongated tubular member sealingly attached to said outer diameter of said inflatable collar,
   c. collecting means associated with the end of said elongated tubular member remote from said inflatable collar for collection of urine discharged from said penis, and
   d. means for inflating said collar.

2. The collecting device of claim 1 in which said elongated tubular member forms a continuous channel from said inflatable collar to said collecting means so that there is no leakage of said urine during use.

3. The collecting device of claim 1 wherein said means for inflating said collar comprises valve means, and including channel means for connecting said valve means to said inflatable collar.

4. The collecting device of claim 3 wherein said collecting means comprises bag means, and wherein said channel means comprises a keyway located along the inner wall of said bag means and said elongated tubular member.

5. The collecting device of claim 1 prepared from a thin medically-approved pliable material.

6. The collecting device of claim 5 wherein said pliable material comprises a plastic selected from the group consisting of polyvinylchloride and urethane.

7. The collecting bag of claim 1 including a rigid cylindrical support collar maintained within said elongated tubular member.

8. A urine-collecting device for use in the continuous collection of urine from a male penis, comprising
 a. an inflatable collar for attachment to a penis, so that upon its inflation, said collar is firmly anchored to said penis, said inflatable collar including an inner diameter and an outer diameter,
 b. an elongated tubular member sealingly attached to said outer diameter of said inflatable collar,
 c. collecting means comprising bag means associated with the end of said elongated tubular member remote from said inflatable collar for collection of urine discharged from said penis, and
 d. means for inflating said collar comprising valve means, and including channel means for connecting said valve means to said inflatable collar, said channel means comprising a key way located along the inner wall of said elongated tubular member, so that said elongated tubular member can form a continuous channel from said inflatable collar to said collecting means so that there is no leakage of said urine during use.

9. The collecting bag of claim 8 including a rigid cylindrical support collar maintained within said elongated tubular member.

10. The collecting device of claim 8 prepared from a thin medically-approved pliable material.

11. The collecting device of claim 10, wherein said pliable material comprises a plastic selected from the group consisting of polyvinyl chloride and urethane.

* * * * *